United States Patent [19]
Dorsel et al.

[11] Patent Number: 5,945,679
[45] Date of Patent: Aug. 31, 1999

[54] APPARATUS FOR SCANNING A CHEMICAL ARRAY

[75] Inventors: Andreas Dorsel, Menlo Park; Steven M. Lefkowitz, Millbrae; John W. Sadler, Belmont, all of Calif.

[73] Assignee: Hewlett-Packard Company, Palo Alto, Calif.

[21] Appl. No.: 09/132,068

[22] Filed: Aug. 17, 1998

Related U.S. Application Data

[62] Division of application No. 08/790,775, Jan. 30, 1997, Pat. No. 5,837,475.

[51] Int. Cl.⁶ .................................................. G01N 21/64
[52] U.S. Cl. ...................................... 250/458.1; 250/459.1
[58] Field of Search ............................... 250/459.1, 458.1

[56] References Cited

U.S. PATENT DOCUMENTS

| | | |
|---|---|---|
| Re. 33,241 | 6/1990 | Tsuchiya . |
| 4,611,920 | 9/1986 | Tsuchiya . |
| 4,631,581 | 12/1986 | Carlsson . |
| 4,786,170 | 11/1988 | Groebler . |
| 5,108,179 | 4/1992 | Myers . |
| 5,117,466 | 5/1992 | Buican et al. . |
| 5,143,854 | 9/1992 | Pirrung et al. . |
| 5,304,810 | 4/1994 | Amos . |
| 5,329,352 | 7/1994 | Jacobsen . |
| 5,381,224 | 1/1995 | Dixon et al. . |
| 5,444,527 | 8/1995 | Kosaka . |
| 5,459,325 | 10/1995 | Hueton et al. . |
| 5,705,821 | 1/1998 | Barton et al. ............... 250/458.1 |

FOREIGN PATENT DOCUMENTS

| | | |
|---|---|---|
| 2537098 | 3/1976 | Germany . |
| 2947459 | 5/1981 | Germany . |
| 2-218941 | 8/1990 | Japan ........................... 250/458.1 |
| WO89/10977 | 11/1989 | WIPO . |
| WO 91/07087 | 5/1991 | WIPO . |
| WO 92/10587 | 6/1992 | WIPO . |
| WO92/10588 | 6/1992 | WIPO . |

OTHER PUBLICATIONS

Sharonov et al., "Confocal Spectral Imaging Analysis in Studies of the Spatial Distribution of Antitumour Drugs with Living Cancer Cells", Anal. Chim. Acta 290, pp. 40–47, May 20, 1994.

Diamandis, "Immunoassays with Time–resolved Florescence Spectroscopy: Principles and Applications", Clin Biochem, vol. 21 (Jun. 1988), pp. 139–150.

Fodor, Stephen P.A. et al., "Light–Directed, Spatially Addressable ...", Research Article, Science, vol. 251, (Feb. 15, 1991), pp. 767–773.

*Primary Examiner*—Constantine Hannaher

[57] ABSTRACT

A technique for analyzing analytes in a chemical array having a plurality of pixels is provided. The apparatus of the technique contains a light source for irradiating a light beam at the pixels individually, a controller for controlling the relative position of the light source to the array, and a detector for detecting fluorescence resulting from irradiation. The controller controls the light beam generated by the light source to irradiate a first number of pixels sequentially in the array and repeating one or more times the sequential irradiation before irradiating a second number of pixels, the pixels of which are different from those of the first number of pixels. The first number of pixels includes more than one pixel but less than the total number of pixels in the array.

21 Claims, 3 Drawing Sheets ns to a
large number of applications, from DNA and protein
sequencing to DNA fingerprinting and disease diagnosis.

APPARATUS FOR SCANNING A CHEMICAL ARRAY

CROSS REFERENCE TO RELATED APPLICATION

This is a divisional of application Ser. No. 08/790,775 filed on Jan. 30, 1997, now U.S. Pat. No. 5,837,475 issued on Nov. 17, 1998.

FIELD OF THE INVENTION

The present invention relates to detecting chemicals in a chemical array and, more particularly, to improving the signal to noise ratio by repeating scanning of the pixels of the array.

BACKGROUND

Recently, chemical arrays, more particularly, biomolecular arrays, have been successfully created. For example, Fodor, et al., "Light-directed, Spatially Addressable Parallel Chemical Synthesis," *Science*, Vol. 251, 767–773 (1991) disclose high density arrays formed by light-directed synthesis. The array was used for antibody recognition. Biomolecular arrays are also described by E. Southern (PCT Publication WO 89/10977) for analyzing polynucleotide sequences. Such biomolecular arrays lend themselves to a large number of applications, from DNA and protein sequencing to DNA fingerprinting and disease diagnosis.

A typical approach for synthesizing a polymer array on an optical substrate is described by Fodor et al. (1991) *supra*; PCT publications WO 91/07087, WO 92/10587, and WO 92/10588; and US Pat. No. 5,143,854. In such arrays, different receptors are synthesized onto a substrate using photolithographic techniques. Ligands are washed over the array. Either the ligand is fluorescently labeled or an additional fluorescently labeled receptor is also washed over the array. The result is that fluorophores are immobilized on those pixels where binding has occurred between the ligand and the receptor(s). In general, a chemical array is illuminated with radiation that excites the fluorophores. The pattern of bright and dark pixels is recorded. Information about the ligand is obtained by comparing this bright-dark pattern with known patterns of surface bound receptors.

In many application, e.g., in analyzing the human genome, it is often necessary to scan a large number of array elements. Therefore, the ability to read a chemical array with a large number of elements within a short time is highly desirable. Lasers have been used to impinge on chemical array elements with a small spot size beam of high intensity.

SUMMARY

The present invention provides an apparatus and technique for analyzing chemicals in a chemical array that is scanned, i.e., read by irradiating and detecting any resulting light interaction such as fluorescence, in lines of pixels. Some of the pixels are suspected to contain target chemicals that contain a fluorescent material. The apparatus includes a light source, a controller, and a detector. The light source is used for irradiating a light beam at the pixels individually. The light source may contain a light generator, such as a laser, and a mechanism for directing a light beam from the light generator, such as a scanner. The controller controls the relative position of the light source to that of the pixels such that the light source directs the light beam to irradiate pixels in a set sequentially in the array. The sequential irradiation is repeated on the set of pixels one or more times before a second set of pixels, which contains pixels different from those in the first set of pixels, are irradiated. The first set of pixels has more than one pixel but less than the total number of pixels in the array. The detector is used for detecting fluorescence resulting from the irradiation on the array.

The apparatus and technique of the present invention can be advantageously used to analyze chemical arrays, particularly large chemical arrays that contain thousands or millions of small pixels, when scanned. By allowing adequate time for the dye molecules in the pixels to recover from metastable states, which can not fluoresce, more signals can be obtained to improve the signal-to-noise ratio without increasing the excitation beam intensity. However, by reducing the time before repeating the irradiation of the a pixel and the distance traversed by the beam between re-irradiations (i.e., repeating irradiation) of a pixel, more accurate superposition is achieved, leading to more reliable data.

BRIEF DESCRIPTION OF THE DRAWINGS

The following figures show the embodiments of the present invention to better illustrate the apparatus and technique of the present invention. In these figures, like numerals represent like features in the several views and the drawings are not drawn to scale for the sake of clarity.

DETAILED DESCRIPTION OF THE INVENTION

The present invention provides an improved technique for analyzing chemical array by repeating illumination and detecting the resulting fluorescence of a set of pixels in the array before moving to another set of pixels. In each set of pixels, all the pixels are illuminated sequentially before repeating. This improves the signal to noise ratio by allowing adequate time for the dye to recover from metastable states before it is illuminated again.

As used herein, an "array" is an arrangement of objects in space in which each object occupies a separate predetermined spatial position. Each of the objects or array elements (which may contain many pixels when scanned with light pulses) in the array in an apparatus of this invention contains one or more species of binder chemical moieties for binding specific analytes, such that the physical location of each species of analytes is known or ascertainable. "Pixel" are spots of an array, which spots are illuminated and the resultant light from the spots is detected as discrete elements to form an image pattern when the array is being analyzed. An "analyte" is a molecule whose detection in a sample is desired and which selectively or specifically binds to a binder chemical moiety, such as a molecular probe. An analyte can be the same or a different type of molecule as the molecular probe to which it binds.

Figure 1:
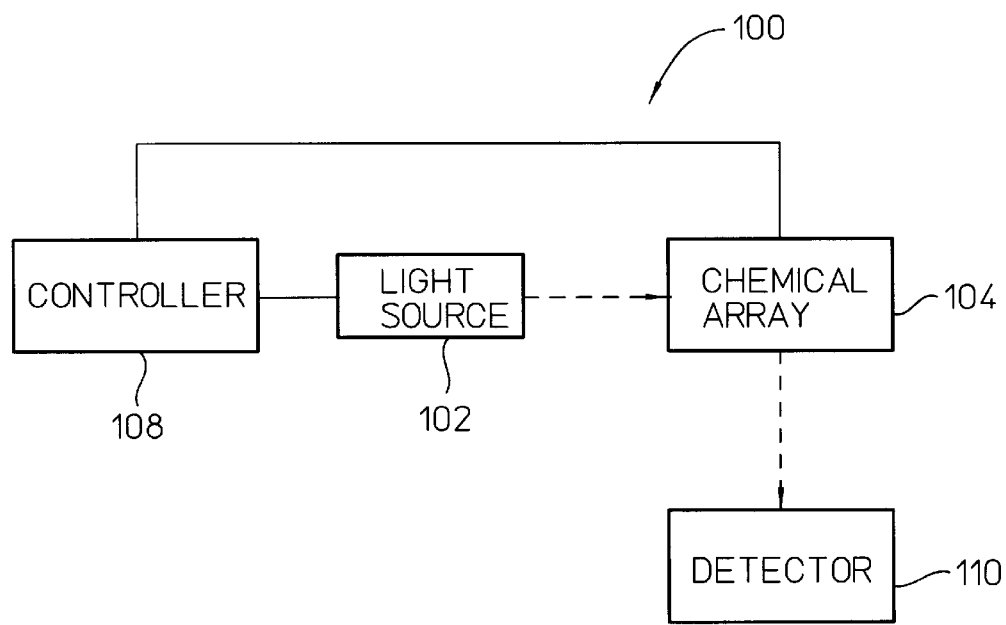
FIG. 1 shows a schematic representation of an apparatus according to the present invention.

FIG. 1 shows a schematic representation of an apparatus for analyzing chemical arrays according to the present invention. The apparatus 100 contains a light source (e.g., laser) 102 for emitting a light of a wavelength and with sufficient intensity to cause fluorescence in a selected fluorescent material. Often, the excitation light intensity is sufficiently high such that the dye used in the chemical array 104 approaches metastable state saturation, i.e., some of the dye molecules cross into metastable states. A controller 108 directs the light from the light source 102 to impinge on the elements of the array one pixel at a time. This can be accomplished, for example, by using a controller to change the relative position of the light source 102 to the chemical array 104, e.g., by moving the light generator (e.g., a laser) in the light source, moving the chemical array, or steering a light beam, e.g., by using a scanner, such that different pixels can be illuminated at different time. Typically, the light beam is directed by translation of the array on an object table 217 (not shown in FIG. 1 but shown in FIG. 2) or scanning the light beam with a beam scanner. The dye, when excited by the excitation light from the light source 102, emits fluorescence, which is detected by a detector 110. The fluorescence intensity can also be measured.

Figure 2:
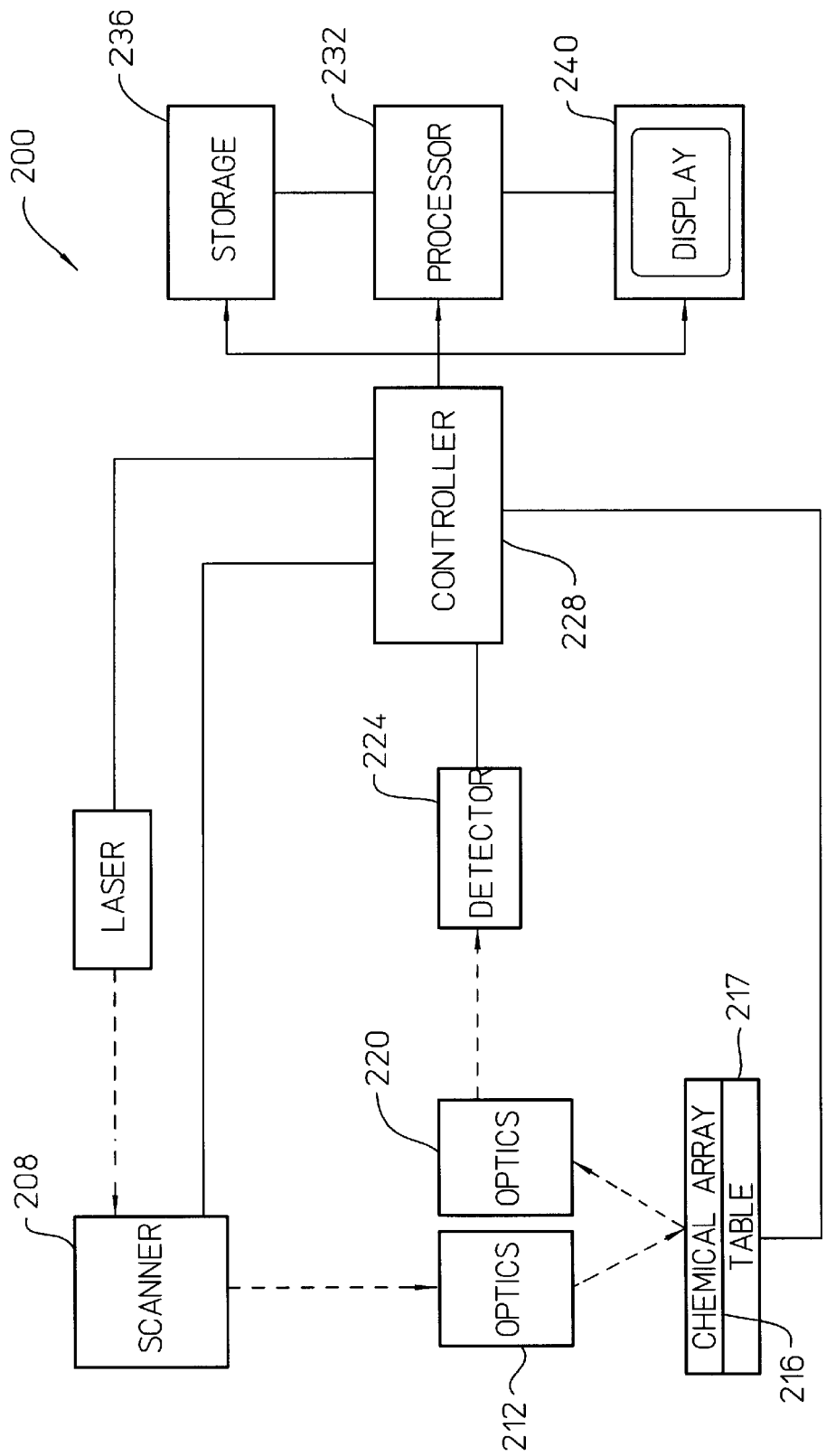
FIG. 2 shows a schematic representation of further details of an apparatus according to the present invention.

FIG. 2 shows in further detail an embodiment of the apparatus of FIG. 1. The apparatus 200 has a laser 204, which emits an excitation laser beam. A scanner 208 directs the laser beam through an optics system 212 to a chemical array 216 to cause fluorescence. The optics system 212 can contain, for example, collimating optics such as lenses and prisms to focus the laser light on the pixels in the chemical array.

Fluorescent light resulting from the array being irradiated by the laser light is collected by an optics system 220, which can contain, for example, lenses and prisms to direct the fluorescent light to a detector 224. The optics systems 220 can also contain filters and apertures to filter out unwanted light such as excitation light. A controller 228 is electrically connected to the detector 224 for collecting electrical signals generated in the detector as a result of fluorescent light impinging on the detector. The controller 228 is connected to the scanner 208 such that each fluorescent light signal received by the detector 224 can be traced to the pixel from which the fluorescent light signal is generated. The controller 228 is further connected to the laser 204 and may be used to control the laser to emit light pulses of a specific duration. The scanner 208 is used to move the laser beam from a pixel to another between pulses. However, if desired, the laser can emit a continuous beam as the scanner directs the laser beam from pixel to pixel. Alternatively, instead of scanning, i.e., moving, the excitation beam, the chemical array 216 can be controlled to translate to position different pixels under the focused excitation beam at different times. Another alternative is to control to physically move the laser 204 to direct the laser beam at different pixels.

The data of signals received by the controller 228 can be processed to determine the presence or quantity of analytes in the pixels. To achieve this, the controller 228 can contain a microprocessor or a computer to process the information on pixel locations and fluorescence. The signals from the detector 224 or the information from the controller 228 can further be transmitted to another processor 232 for further data processing and to a storage device 236, such as disk, tapes, compact disk, and the like. The information from the controller 228 or processor 232 can also be displayed in a display device 240 such as a cathode ray tube, plotter, printer, and the like. If desired, different computers and microprocessors can be used to control the light beam/pixel relative position and for linking the data of pixel position and fluorescence pattern.

METHOD OF READING ARRAY

Figure 3:
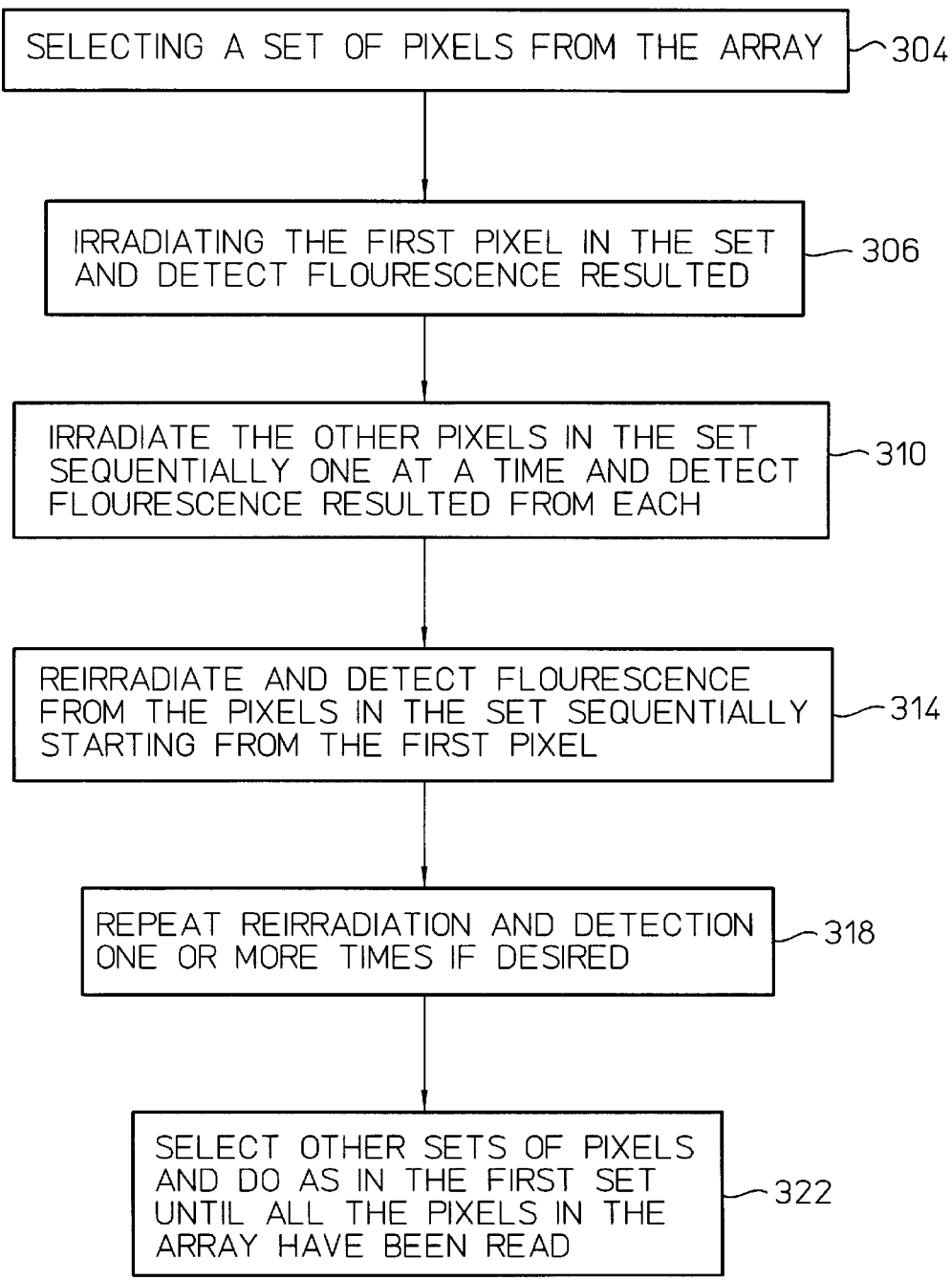
FIG. 3 is a flow diagram showing the process of reading a chemical array according to the present invention.

FIG. 3 shows the technique for analyzing, i.e., reading, or scanning (i.e., read) pixels in a chemical array according to the present invention. Typically the array includes array elements, which when read by irradiation and detection of fluorescence, result in pixels that are arranged in rows and columns, each of which may be considered a line. For illustration, we call a row a line. A set of pixels are selected from the array (step 304). The first pixel in the set is irradiated with a laser beam for a specific duration, e.g. a few microseconds and the resultant fluorescence is detected or measured (step 306). The other pixels in the set are similarly treated, i.e., irradiated and the resultant fluorescence (step 310) detected sequentially one pixel at a time. After the last pixel in the set has been read once by irradiation and detection the pixels are read again one or more times (steps 314 and 318) in a manner similar to the first reading. Other sets of pixels in the array are selected and read as done with the first set until all the pixels have been read (step 322). Generally, this means all the array elements have been read.

Preferably, each of the sets includes pixels that are physically close together so that the movement of the actuating mechanism, e.g., scanner, for moving the relative location of light beam to pixels, is not extensive when moving from pixel to pixel in irradiation and re-irradiation. For example, the set can be a number of pixels (i.e., a subset of pixels) in a line. More preferably, the set is a line (e.g., a row or a column) to facilitate the smooth movement of scanning mechanism to scan sequentially the pixels in the set. If desired, the set can include a portion of a line or more than one line. As previously stated, the number of pixels in a set is selected such that adequate time is allowed for the recovery of the pixels from the metastable states.

SELECTING TIME BEFORE REPEATING IRRADIATING A PIXEL

Figure 4:
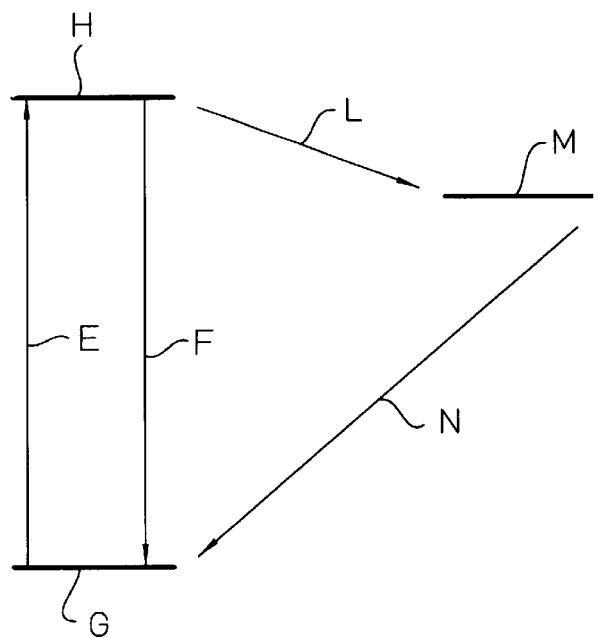
FIG. 4 shows a schematic representation to illustrate some of the energy levels of a dye.

In a laser induced fluorescence scanner with small spot size (e.g., about 3 $\mu$m FWHM Gaussian beam), the laser light excites the fluorophore (i.e., dye) molecules and cause fluorescence. The fluorescence is detected to indicate the presence of the fluorophore molecules, and therefore the presence of analytes that are attached to fluorophore molecules. FIG. 4 is a schematic representation showing the energy level transition when a dye is excited. When a dye molecule absorbs laser light (arrow E), it is excited from the ground state energy level G, to the energy level H. From energy level H the dye molecule falls back to the ground state (arrow F), releasing light as fluorescence.

To produce better signals, fairly high intensity laser is used, since to a degree higher intensity excitation light (i.e., light from the laser) produces more fluorescence photons. Because of the intensity of the laser light impinging on the dye, the dye molecules may, depending on the nature of the particular dye, cross (e.g., from the exited energy level H) into metastable state(s) (or long-life-quasi-stable-state(s)), such as the triplet state. As used herein, the term "metastable state," or "long-life-quasi-stable-state" of a dye molecule refers to an energy state in which the dye molecule has higher than the ground state energy level but loses its energy, converting to the dye ground state, an order of magnitude or more slower than the singlet state fluorescence. Depending on the particular dye, many different metastable states are possible. An important example of a metastable state is the triplet state. Other metastable states include the biradical state, and the ion-pair state. Although many metastable states may be possible, for the sake of clarity, in FIG. 4, the metastable states are shown as M, to which transition from energy level H is represented by arrow L. At their metastable states, the dye molecules convert back to the ground state much more slowly than in the singlet state fluorescence, which is shown by arrow F. From the metastable states, the fluorescent material (i.e., dye molecules) does not release light of a wavelength same as that of the fluorescence of arrow F. Therefore, any dye molecule that crosses to the metastable state is lost to fluorescence. Since a dye molecule at a metastable state cannot fluoresce, this phenomenon appears as saturation of the fluorescence signal. In this situation, increasing laser power, i.e., the intensity of illumination on an array element, will not increase the number of detected fluorescence photons proportionally.

For systems limited by photon shot noise in their performance, when saturation is occurring, the signal-to-noise ratio can only be increased marginally, if at all, by scanning more slowly or with higher illumination power. In the present invention, we scan a set (or a number) of pixels in the chemical array two ore more times to increase the signal-to-noise ratio. Furthermore, we wait for a period of time for the molecules in the dye in a pixel to recover sufficiently, preferably substantially, from their metastable states before re-irradiating the pixel. To this end, a set, i.e., a number, of pixels are irradiated sequentially, each for short duration (e.g., a few microseconds) such that by the time the last pixel in the set is irradiated, the first pixel has recovered from the metastable state.

The time period (herein referred to as the "rest period") to be selected for the dye in a pixel to recover from the metastable states before re-irradiating depends on the nature of the dye. Many commonly used dyes have recovery time constants of metastable states in the range of about $10^{-5}$ S to $10^{-1}$ S. For this reason, a rest period of about $10^{-5}$ S to $10^{-1}$ S would be adequate for the dye in a pixel to substantially recover from its metastable states. In contrast, the fluorescence time constant is in the range of nanoseconds. Generally, the rest period of a few of the commonly used dyes are known in the art. The rest period of a dye can also be determined by a method as described below. The number of pixels to be included in a set depends on the illumination time for a pixel and the recovery time (or rest period) of the dye. Generally, 100 or more of pixels, preferably more than about 1000 pixels, are included in a set of pixels to be read sequentially before re-irradiation.

To determine the rest period of a dye, the following technique can be used. The dye of interest is subjected to light from an irradiation source, which is turned on rapidly relative to the dye rest period while the temporal evolution (i.e., the time dependence of the fluorescent intensity) of the fluorescent intensity is monitored. The fluorescent intensity is the highest initially but it decreases to a lower level over time. The time to reach the lower intensity level is closely related to the dye rest period. Decrease in the fluorescent intensity reflects the level of saturation. Data obtained can be fitted to a mathematical model to obtain time constants of the change in intensity. Methods of modeling to obtain time constants are known in the art. Generally, the dye is considered to have sufficiently recovered from the metastable states after about one time constant. It is considered to have substantially recovered from the metastable states after about 2 time constants.

Examples of suitable dyes (i.e., fluorescent material) that can be used as labels for the present invention include dyes well known to one skilled in the art, such as fluoresceins, TEXAS RED, ethidium bromide, chelated lanthanides, rhodamines, indocyanines, carbocyanines, oxazines, organometallics, and metal atom cluster compounds. The rest period, i.e., time needed for recovery from the metastable states of these dyes, can be determined with the technique described in the above.

A variety of suitable light-emitting devices can be used as the light generator in the light source. Such light-emitting devices are known in the art. They include, for example, light emitting diode (LED) and lasers, such as diode lasers, gas lasers, e.g., HE-NE laser, Ar ion laser, frequency doubled Neodynium-glass laser, nedium YAG laser, fiber laser, or other solid-state lasers. The pixels in the array can be arranged in a flat pattern. An alternative is arranging the pixels in a circular pattern as on a cylindrical surface. Generally, the pixels are held in a pattern of rows and columns. Since we know the origin of each pixel, we know the binder chemical moieties in the pixel. If fluorescence is detected for the pixel, we will know the identity of the analyte bound to that pixel.

ARRAY LIGHT DETECTION

A detector is used for detecting the light resulting from fluorescence in the array. For example, a single element optical detector, e.g., a PNT photomultiplier tube, may be used. Since the time of a light beam being directed at any particular pixel is known and the illumination of different pixels are temporally spaced apart, the corresponding fluorescence detected will indicate the presence of fluorescent material in the pixel. An alternative detector is an array detector in which more than one detector element is used to over-sample the target chemicals, permitting the discrimination against non-uniformities. One example of an array detector is a solid-state semi-conductor device, such as a charge-coupled device (CCD) array.

The excitation light from a light source impinges on the fluorescent material bound to the analyte in the array and causes it to emit light as fluorescent light. Only pixels with a fluorescent material will emit fluorescence signal. The detected fluorescent signals are identified with electronic excitation for light sources and processed, preferably by an electronic processing unit, such as a microprocessor or a computer.

As previously stated, by analyzing the pattern of the fluorescence light in the array, the identity of the analytes in the sample can be determined. Detecting fluorescence with a suitable detector will result in the pattern of fluorescence, in which certain locations in the pattern show fluorescence and certain locations do not. The identity of an analyte on a particular pixel in the array can be determined by detecting the location of the fluorescence in the pattern and linking this location with data concerning the identity of binder chemical moieties and pixel positions in the array. There are various methods for linking such data with the chemical array. For example, the data can be physically encoded on the array's housing or stored separately in a computer.

The present technique of irradiation and detection has a great advantage over techniques that require re-irradiation after reading each pixel or re-irradiate only after the whole array has been read. If the re-irradiation of a pixel is done immediately after the pixel has been irradiated, the dye molecules in the pixel may not have enough time to recover sufficiently from the metastable states and fluorescence is less than optimal due to the presence of metastable states, which do not fluoresce. However, if re-irradiation is done only after the whole array or a large section, such as half, of the array has been irradiated, the actuating or beam steering mechanism would have to move a substantial distance and wait a long time before going back to the first array. This is particularly true for large arrays (e.g., those having more than a thousand, or even having thousands of pixels in a row or column) with small and closely adjacent pixel dimensions of today. For example, the dimension of a pixel can be as small as 3 μm across. In traversing a substantial distance and waiting a long time, the original pixels positions may not be reestablished (i.e., superpositioned) easily. For example, the temperature may have changed, thereby causing the array to change in size. For example, thermal expansion can occur if the array has been stored in below room temperature before reading in room temperature. In the present invention, adequate time is taken for the dye in a pixel to recover from the metastable states, but not so much time that it increases substantially the difficulty in superpositioning the laser beam at the original locations. The result of rescans (i.e., re-readings) can be added or averaged on line to reduce the amount of data to be stored.

As previously stated, the control of the actuating or beam-steering mechanism, e.g., the scanner for moving the laser beam, the actuating system for moving the array, or the actuator that moves the laser, can be done by a computer. Generally, a computer program, or software can be implemented to accomplish such control, as well as the detection and measurement of the fluorescence. The control of actuators, scanners, etc., are well known in art.

In the analysis of data, the fluorescence intensity of each reading of a pixel is stored in the memory of a computer (which can also be a microprocessor). After each re-irradiation and re-detection, the memory is updated by summing the old and new fluorescence data for each pixel. In the absence of bleaching of the dye, the signals increase proportionally to the number n of the repeated readings and the signal-to-noise ratio scales as the square root of n.

For illustration purposes, the following example is given. However, one skilled in the art will be able to adapt the disclosed example for other applications. A UNIPHASE (San Jose, Calif.), model 2211-20SLE laser operating at an output power of 10 mW, wavelength of 488 nm, and a focal spot of 3 μm full-width-half-maximum (FWHM) was used to scan a chemical array having 5000 pixels in a row. The irradiation duration was at least 5 μs for each pixel, for example, 6 μs. A fluorescein, which has a fluorescence lifetime in the order of nanoseconds, was the dye for labeling the analytes. The time needed for recovery from the metastable states of the fluorescein was in the order of milliseconds. By scanning one line, i.e., 5000 pixels, before re-irradiation, the line time, i.e., time needed to finish a line before repeating, is at least about 30 ms, which is ample for the fluorescein to recover from its metastable states.

Although the illustrative embodiments of the apparatus of the present invention and the methods of making and using the apparatus have been described in detail, it is to be understood that the above-described embodiments can be modified by one skilled in the art, especially in sizes and shapes and combination of various described features without departing from the scope of the invention. Although the theory outlined in the present disclosure is believed to be accurate, the application of the present invention is not dependent on any theory described herein.

What is claimed is:

1. An apparatus for analyzing chemicals in an array having a plurality of array elements some of which are suspected to contain fluorescent material, comprising:

(a) a light source for irradiating a light beam at the elements in individual pixels, the pixels being arranged in lines;

(b) computer means for controlling the relative position of the light source to the array such that the light source directs the light beam to irradiate a first number of pixels sequentially in the array and repeating one or more times the sequential irradiation before irradiating a second number of pixels, the pixels of which are different from the first number of pixels, the first number of pixels having more than one pixel and less than the total number of pixels in the array such that a period elapses adequate for the fluorescent material in a pixel to recover from a metastable state before the pixel is irradiated again; and (c) detector for detecting fluorescence resulting from the irradiation.

2. The apparatus according to claim 1 wherein the means for controlling is adapted to direct light at the first number of pixels being irradiated before repeating such that a period elapses adequate for the fluorescent material in a pixel to substantially recover from its triplet excited state before the pixel is irradiated again.

3. The apparatus according to claim 1 wherein at least a portion of the light source is movable and the means for controlling is adapted to move the at least a portion of the light source to direct the light beam from pixel to pixel to irradiate the pixels.

4. The apparatus according to claim 1 wherein the controlling means is adapted to control the light source to irradiate the pixels in a line sequentially and repeat one line at a time from adjacent line to adjacent line, without irradiating a line after another line has been irradiated thereafter.

5. The apparatus according to claim 1 further comprising a means to sum fluorescence signals detected from a pixel by the detector during repeated irradiation of the pixel.

6. The apparatus according to claim 1 wherein the light source is adapted to emit a light suitable for causing fluorescence in a fluorescent material selected from the groups consisting of fluoresceins, TEXAS RED, ethidium bromide, chelated lanthanides, rhodamines, indocyanines, carbocyanines, oxazines, organometallics, and metal atom cluster compounds.

7. The apparatus according to claim 1 further comprising an object table on which the array can be placed for the translation of array wherein the means for controlling is adapted to control the object table to move the array to position the pixels to be irradiated from pixel to pixel.

8. The apparatus according to claim 1 further comprising an object table on which an array having lines of pixels which have 100 or more pixels per line can be placed, wherein the means for controlling is adapted to control the relative movement of the array to the light source to irradiate from pixel to pixel.

9. The apparatus according to claim 1 further comprising an object table for holding an array having a plurality of lines of pixels, each line have 100 or more pixels, wherein the means for controlling is adapted to control movement of the array to irradiate from pixel to pixel.

10. An apparatus for analyzing chemicals in an array having a plurality of array elements some of which are suspected to contain fluorescent material, the apparatus comprising:

(A) light source for irradiating a light beam at the elements in individual pixels, the pixels being arranged in lines;

(B) detector for detecting fluorescence resulting from the irradiation;

(C) processor for controlling the relative position of the light source;

(D) program storage medium that tangibly embodying a program code means readable by the processor for causing the processor to analyze the chemical array, the program code means including:

(i) code means for controlling the relative position of the light source to the array to irradiate a first number of pixels sequentially in the array elements and to detect the fluorescence resulting from the irradiation in the pixels, the first number of pixels being more than one pixel and less than the total number of pixels in the array and such that a period elapses adequate for the fluorescent material in a pixel to recover from a metastable state before the pixel is irradiated again; and (ii) code means for controlling the relative position of the light source to the array to repeat the irradiation and detecting on the first number of pixels one or more times before irradiating pixels of a second number of pixels that are different from the pixels of the first number of pixels in the array.

11. The apparatus according to claim 10 further comprising code means for selecting the first number of pixels based on information on the adequate period for the fluorescent material in a pixel to recover from a metastable state.

12. The apparatus according to claim 10 wherein the code means for controlling the irradiation of the first number of pixels controls the irradiation before repeating such that a period elapses adequate for the fluorescent material in a pixel to substantially recover from its triplet excited state before the pixel is irradiated again.

13. The apparatus according to claim 10 wherein the code means for controlling to repeat the irradiation controls to move an irradiating light beam from pixel to pixel in a line of pixels and repeating the irradiating of the same line at least once before moving on to another line of pixels.

14. The apparatus according to claim 10 wherein the first number of pixels is the number of pixels in a first line and the second number of pixels is the number of pixels in a line adjacent to the first line in the array, each line having more than 100 pixels.

15. The apparatus according to claim 10 wherein the code means for controlling to repeat the irradiation controls to irradiate pixels in a line sequentially and to repeat before irradiating another line, substantially all of the lines are irradiated one line at a time from one adjacent line to the next, for all the lines of pixels without re-irradiating a line once a different line has been irradiated thereafter.

16. The apparatus according to claim 10 wherein the code means controls to irradiate an adequate of number pixels in a line such that $10^{-5}$ second to $10^{-1}$ second has elapsed before a pixel is re-irradiated.

17. The apparatus according to claim 10 wherein the light source is adapted to emit a light suitable for causing fluorescence in a fluorescent material selected from the groups consisting of fluoresceins, TEXAS RED, ethidium bromide, chelated lanthanides, rhodamines, indocyanines, carbocyanines, oxazines, organometallics, and metal atom cluster compounds and wherein the code means further comprising code means for selecting the first number of pixels based on information on the adequate period for the selected fluorescent material in a pixel to recover from a metastable state.

18. An apparatus for analyzing chemicals in an array having a plurality of array elements some of which are suspected to contain fluorescent material, the apparatus comprising:

(A) light source for irradiating a light beam at the elements in individual pixels, the pixels being arranged in lines;

(B) detector for detecting fluorescence resulting from the irradiation;

(C) processor for controlling the relative position of the light source;

(D) program storage medium tangibly embodying a program code means readable by the processor for causing the processor to analyze the chemical array, the program code means including:

(i) code means for controlling the relative position of the light source to the array to irradiate a line of pixels sequentially in the array elements and to detect the fluorescence resulting from the irradiation in the pixels, the line of pixels having more than 100 pixels and less than the total number of pixels in the array, the number of pixels in a line being sufficiently large such that a period would elapse adequate for the fluorescent material in the pixel first irradiated to recover from a metastable state before the whole line has been irradiated;

(ii) code means for controlling the relative position of the light source to the array to repeat the irradiation and detect on the first line of pixels one or more times before irradiating pixels of a second line of pixels, such that $10^{-5}$ second to $10^{-1}$ second has elapsed before a pixel is re-irradiated, and to irradiate and detect in like manner all of the array elements until all the array elements have been irradiated without re-irradiating any line of pixels after another line has been irradiated subsequent to the irradiation of that any line.

19. An article of manufacture comprising a program storage medium, tangibly embodying a program code means readable by a computer for causing the computer to control the analysis of a chemical array by irradiation resulting in fluorescence, the program code means including:

(i) code means for controlling the relative position of a light source to the array to irradiate a first number of pixels sequentially in array elements of the array and to detect the fluorescence resulting from the irradiation in the pixels, the first number of pixels being more than one pixel and less than the total number of pixels in the array and such that a period elapses adequate for the fluorescent material in a pixel to recover from a metastable state before the pixel is irradiated again; and (ii) code means for controlling the relative position of the light source to the array to repeat the irradiation and detecting on the first number of pixels one or more times before irradiating pixels of a second number of pixels that are different from the pixels of the first number of pixels in the array.

20. An apparatus for analyzing chemicals in an array having a plurality of array elements some of which are suspected to contain fluorescent material, comprising:

(A) a light source for irradiating a light beam at the elements in individual pixels, the pixels being arranged in lines;

(B) means for controlling the relative position of the light source to the array such that the light source directs the light beam to irradiate a first number of pixels sequentially in the array and repeating one or more times the sequential irradiation before irradiating a second number of pixels, the pixels of which are different from the first number of pixels, the first number of pixels having more than one pixel and less than the total number of pixels in the array such that a period elapses adequate for the fluorescent material in a pixel to recover from a metastable state before the pixel is irradiated again; and (C) detector for detecting fluorescence resulting from the irradiation; wherein at least a portion of the light source is movable and the means for controlling is adapted to move the at least a portion of the light source to direct the light beam from pixel to pixel to irradiate the pixels.

21. An apparatus for analyzing chemicals in an array having a plurality of array elements some of which are suspected to contain fluorescent material, the apparatus comprising:

(A) light source for irradiating a light beam at the elements in individual pixels, the pixels being arranged in lines;

(B) detector for detecting fluorescence resulting from the irradiation;

(C) processor for controlling the relative position of the light source;

(D) program storage medium that tangibly embodying a program code means readable by the processor for causing the processor to analyze the chemical array, the program code means including:

(i) code means for controlling the relative position of the light source to the array to irradiate a first number of pixels sequentially in the array elements and to detect the fluorescence resulting from the irradiation in the pixels, the first number of pixels being more than one pixel and less than the total number of pixels in the array and such that a period elapses adequate for the fluorescent material in a pixel to recover from a metastable state before the pixel is irradiated again;

(ii) code means for controlling the relative position of the light source to the array to repeat the irradiation and detecting on the first number of pixels one or more times before irradiating pixels of a second number of pixels that are different from the pixels of the first number of pixels in the array; and (iii) code means for selecting the first number of pixels based on information on the adequate period for the fluorescent material in a pixel to recover from a metastable state.

* * * * *